United States Patent [19]
Zurek et al.

[11] Patent Number: 5,267,571
[45] Date of Patent: Dec. 7, 1993

[54] METHOD FOR TESTING ADEQUACY OF HUMAN HEARING

[75] Inventors: Patrick M. Zurek, Arlington; William M. Rabinowitz, Bedford, both of Mass.

[73] Assignee: Sensimetrics Corporation, Cambridge, Mass.

[21] Appl. No.: 865,127

[22] Filed: Apr. 8, 1992

[51] Int. Cl.$^5$ ............................................. A61B 5/00
[52] U.S. Cl. ........................................ 128/746; 73/585
[58] Field of Search ................. 128/746; 73/585, 587, 73/589

[56] References Cited

U.S. PATENT DOCUMENTS

| | | | |
|---|---|---|---|
| 4,109,106 | 8/1978 | Voss | 73/585 |
| 4,157,456 | 6/1979 | Voss | 73/585 |
| 4,289,143 | 9/1981 | Canavesio et al. | 128/746 |
| 4,374,526 | 2/1983 | Kemp | 128/746 |
| 4,459,996 | 7/1984 | Teele | 128/746 |
| 4,884,447 | 12/1989 | Kemp et al. | 73/585 |
| 5,063,946 | 11/1991 | Wada | 128/746 |
| 5,105,822 | 4/1992 | Stevens et al. | 128/746 |

Primary Examiner—Stephen C. Pellegrino
Assistant Examiner—Guy V. Tucker
Attorney, Agent, or Firm—Hale and Dorr

[57] ABSTRACT

Multiple single-frequency tones are presented simultaneously to a subject by each of two transducers for the purpose of testing hearing. One transducer is employed to present a plurality of $f_1$ primaries and the other transducer a plurality of $f_2$ primaries so as to make the ratio of $f_2$ to $f_1$ sufficient to produce evoked distortion products by the pair. Proper selection of the frequencies prevents numerous intermodulation products.

7 Claims, 4 Drawing Sheets

METHOD FOR TESTING ADEQUACY OF HUMAN HEARING

BACKGROUND OF THE INVENTION

This invention relates to a system and method for measuring hearing, and more particularly to a system and method for measuring hearing that may be successfully applied to individuals unable to respond to instructions or requests of a person administering the test. The system and method of testing herein described may therefore be applied to the measurement of hearing function in babies, for example, permitting assessment of their hearing at an earlier age than possible when methods or systems are used which depend on communication between tester and subject.

It has been known for hundreds of years that the simultaneous introduction to the ear of two single-frequency sinusoidal tones, known as primary tones, or simply as primaries, which are close both in frequency and in sound pressure level, results in the production of numerous audible intermodulation distortion products. The audible distortion products are caused by nonlinear processes within the ear which are, at the present time, of unknown origin. Typically, the frequencies of the primaries used are in the approximate ratio 1:1.2. It is usual to designate the lower in frequency of the two primaries as $f_1$ and the higher as $f_2$. Of the intermodulation distortion generated by the ear, one in particular, with frequency $2f_1 - f_2$, is normally perceptible to the subject to whom the tones are presented.

In 1979, Dr. David Kemp established that distortion tones produced by the cochlea (in the inner ear) could be detected and measured in the ears of normal-hearing persons by placing a sensitive microphone in the ear canal during presentation of the primaries. Subsequently, Kemp and his colleagues as well as numerous other researchers in various countries have obtained data demonstrating that the absence of measurable distortion tones is associated with hearing impairment in that region of the audible spectrum occupied by the two primary tones and the distortion tone. Such a test is often referred to in the literature as one employing the evoked distortion product (EDP) method.

Prior to his discovery of the physical and measurable character of auditory distortion, Kemp, in 1978, established the detectability of a nonlinear version of an impulsive signal returned, as he characterized it, in the form of a "reflection" from the inner ear, which appeared following a brief time interval after the application to the ear of an acoustic impulse. By applying a series of acoustic impulses to the ear and employing a method of averaging and other signal processing by which the linear components of the echo were cancelled, a practical technique for the assessment of the hearing function of passive subjects was developed. Kemp subsequently devised a system for measurement of the spectral and time-domain properties of the nonlinear echo, then made available to researchers a device to carry out such tests, made and sold by Otodynamics, Ltd. While the impulse/echo technique is not the only method used in research, it has gained wide use, especially in laboratory measurement of the hearing of infants and young children.

The present invention, while not using the impulse/echo method disclosed by Kemp in U.S. Pat. Nos. 4,374,526 and 4,884,447 may be regarded as an improvement over that method in several respects. The present invention, because it provides results more rapidly than the impulse/echo method, is more suitable for application to the screening of infants and young children for hearing impairment than methods based on the prior art, and is a useful technique in the research laboratory to be employed supplementary to such impulse/echo methods.

Referring to FIG. 1, in conducting the EDP test in accordance with the prior art, two primaries are presented to the ear, typically by two small transducers 12, analogous to miniature loudspeakers, each transducer presenting one of the two tones. An EDP is measured by placement of a sensitive microphone 14 in the ear canal 16 of the subject, and the output of the microphone is applied to the input of a spectrum or wave analyzer. Alternatively, the output of the microphone, after appropriate amplification, may be applied to the input terminals of an analog-to-digital converter for conversion to a binary-encoded representation of the output waveform of the microphone, and such representation analyzed by a digital computer program for determination of the spectrum of the microphone output signal.

The use of two transducers for presentation of the primaries is necessitated by the tendency of a single transducer, when multiple tones are applied to its input terminals in electrical form, to generate intermodulation distortion products as components of its acoustic output due to the nonlinear behavior of the transducer. Among these distortion components there are likely to be intermodulation distortion components at the same frequencies as those produced by the ear. The transducer's intermodulation distortion would interfere with the measurement of distortion produced by the ear.

A current limitation of the EDP method stems from the variability of emission measurements in normal-hearing ears. When one pair of primaries is presented to a subject, an EDP may not be detected or may be very low in level, leading to the conclusion by the tester that some impairment of the auditory system exists. In fact, the level of the EDP typically varies with frequency for any subject in a specific manner not predictable by any method now known. Consequently, measurement of one EDP alone may mislead the tester. Until now, the only ways of overcoming this problem were either to employ the impulse/echo method, which is relatively time-consuming and inefficient when compared to the EDP method, or to carry out the EDP method at a large number of frequencies in a sequential manner.

In prior art apparatus for measurement of the EDPs produced by pairs of primaries at frequencies spread over the audible frequency range, results are obtained by presenting one pair of primaries at a time and measuring a single EDP produced by that pair. Insofar as infants and small children tend to move and produce sounds that interfere with testing and produce results that are not usable, testing by use of the prior art must be extended for a period of time sufficient to obtain satisfactory data.

It is, therefore, a principal object of the present invention to provide a system and method for testing hearing that acquires information about hearing functionality simultaneously at multiple frequencies in contrast to the prior art EDP method which detects and measures a single EDP.

Another object of the present invention is to provide a system and method of testing hearing that eliminates the likelihood that when multiple pairs of primaries are employed in an EDP test, interfering intermodulation products will be caused by nonlinear interaction of the primaries radiated by each transducer, causing intermodulation products that would conceal or otherwise interfere with measurement of the EDP.

A further object of the invention is to provide a system and method for testing hearing that is more rapid than the prior art tests, so that much less time is taken to complete testing, thereby reducing the cost of each test without compromising the reliability of the data obtained.

Still another object of the invention is to provide a system and method for testing hearing that increases the reliability of tests made by the EDP method.

Yet a further object of the present invention is to provide a system and method of testing hearing that improves the efficiency of EDP testing by automatically limiting the duration of the EDP test to a time that is reasonable and sufficient for the determination of the functionality of the hearing of the subject.

Another object of the invention is to provide a method of testing hearing that facilitates the design of screening apparatus for testing the hearing of children, which apparatus may be conveniently operated by an individual with minimal training.

SUMMARY OF THE INVENTION

In the present invention, multiple single-frequency tones are presented by each of two transducers, unlike the practice in the prior art, in which each transducer presents only one single-frequency tone. One transducer is employed to present a plurality of $f_1$ primaries, each in a different location of the range of audible frequencies, and the other transducer a plurality of corresponding $f_2$ primaries, each having a frequency with respect to its corresponding $f_1$ so as to make the ratio of frequencies suitable for the production of EDPs by that pair. By selection of an appropriate frequency for each primary in each set, a plurality of pairs may be presented to the ear simultaneously, without encountering the problems caused by the presence of numerous intermodulation products due to the interaction of the multiple primaries issued by the same transducer. This allows a single test to be performed that will simultaneously provide information about hearing function over a range of audible frequencies, rather than only the frequency range covered by one pair of primaries and the resulting single CDT.

Frequencies radiated by each transducer must be selected so that they are in a ratio that avoids the production of such intermodulation products at the same frequencies as the EDPs sought by the procedure.

In addition, a test may be conducted in which the detection and measurement of a plurality of EDPs may be simultaneously undertaken, essentially eliminating the likelihood that an absent or weak EDP at a single frequency will mislead the tester.

These and other objects and features of the present invention will be more fully understood from the following detailed description which should be read in light of the accompanying drawings.

DETAILED DESCRIPTION OF THE PREFERRED EMBODIMENTS

Figure 1:
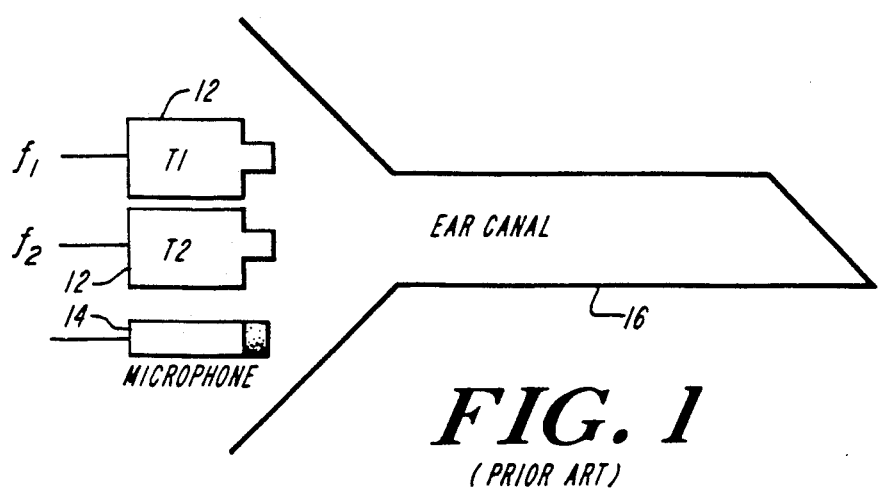
FIG. 1 is a schematic diagram of the apparatus employed in the prior art to conduct tests based on the EDP method.
Figure 2:
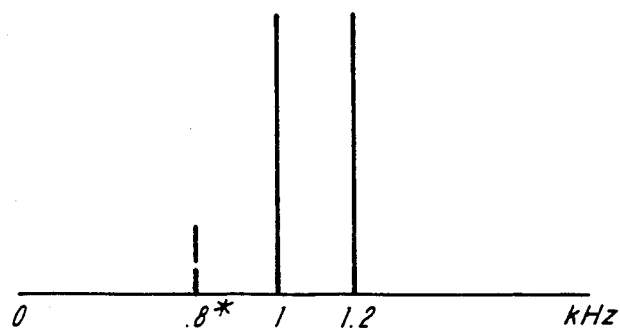
FIG. 2 is a schematic graph of the frequencies and magnitudes of the primaries and the resulting distortion component at $2f_1 - f_2$ determined in a prior art EDP test.
Figure 4:
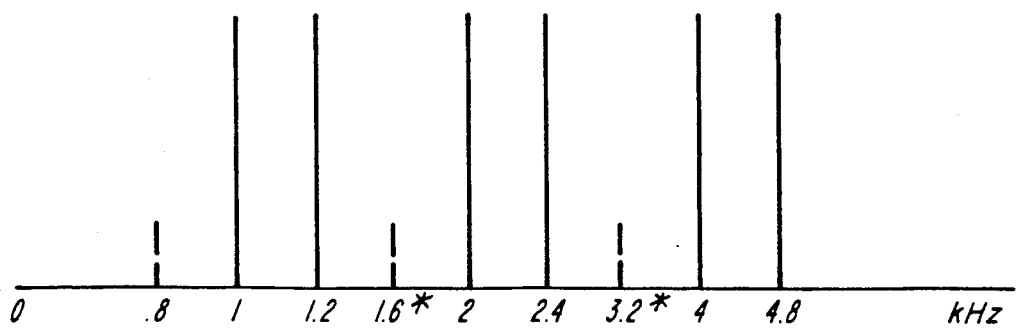
FIG. 4 is a schematic graph of one of numerous configurations of primaries which may be applied to transducers of the present invention to generate in the ear the various EDPs shown, rendered in a manner consistent with the presentation in FIG. 2.
Figure 3:
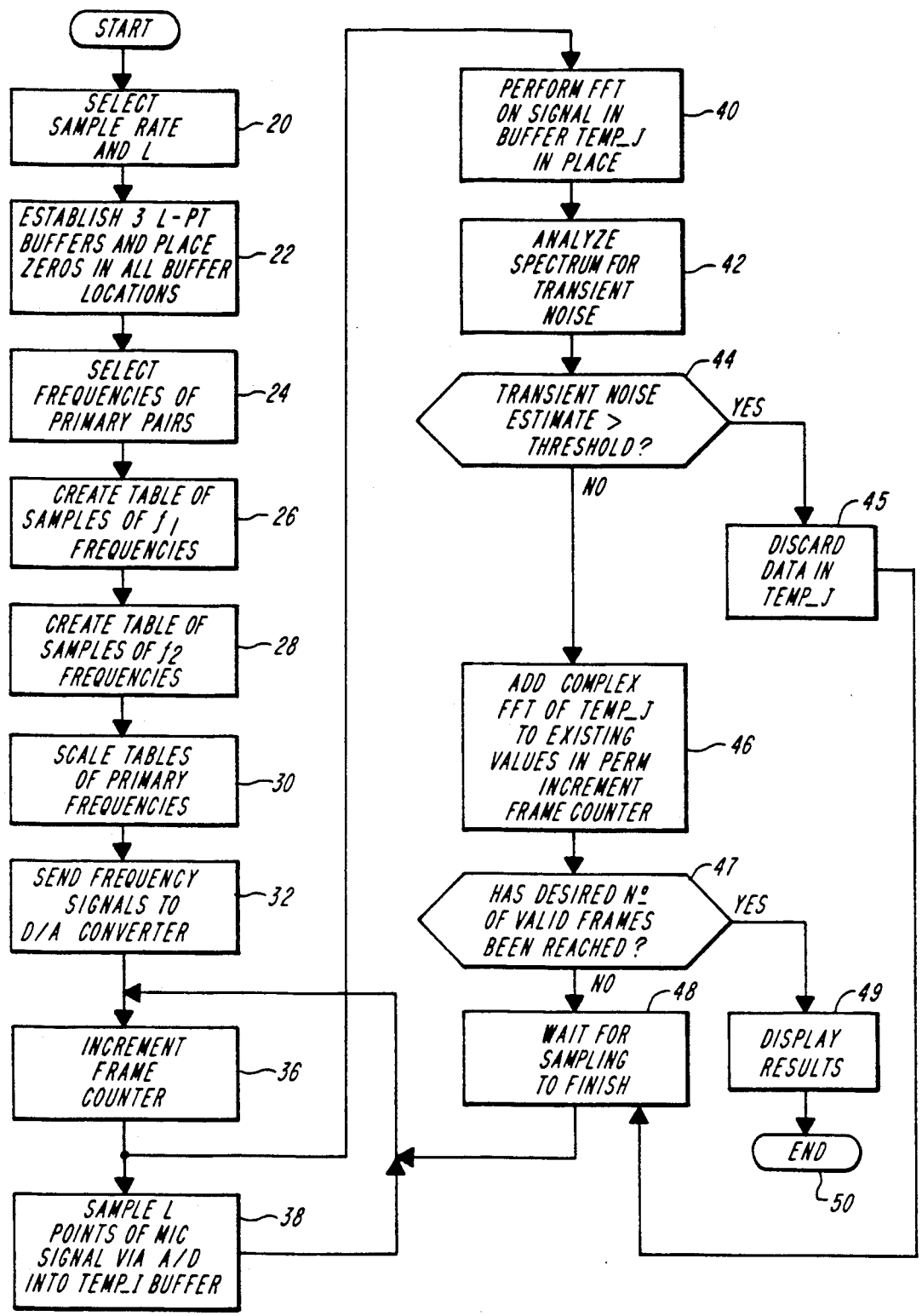
FIG. 3 is a flow chart of the steps for implementing the method of the present invention.
Figure 5A:
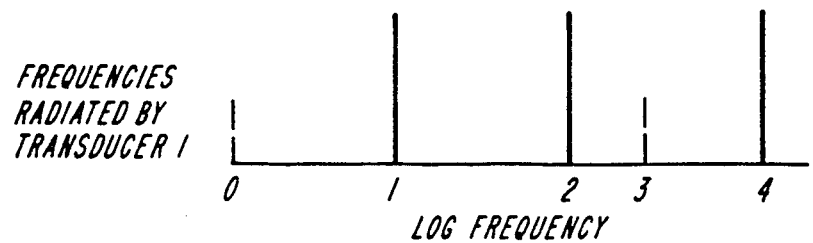
FIGS. 5(a) and 5(b) are graphs of amplitude vs. frequency for signals radiated when each transducer is driven separately, with bold lines indicating the desired primary frequencies and thin lines indicating distortion generated by the transducer.
Figure 5B:
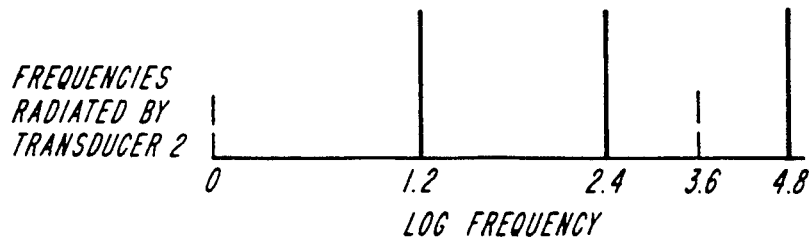
Figure 5C:
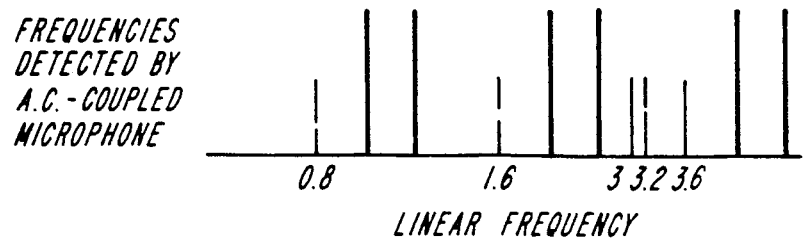
FIG. 5(c) is a graph of amplitude vs. frequency for signals measured when the two transducers are driven simultaneously, with the frequency components including those shown in FIGS. 5(a) and 5(b), along with EDPs, indicated by dashed thin lines.
Figure 6:
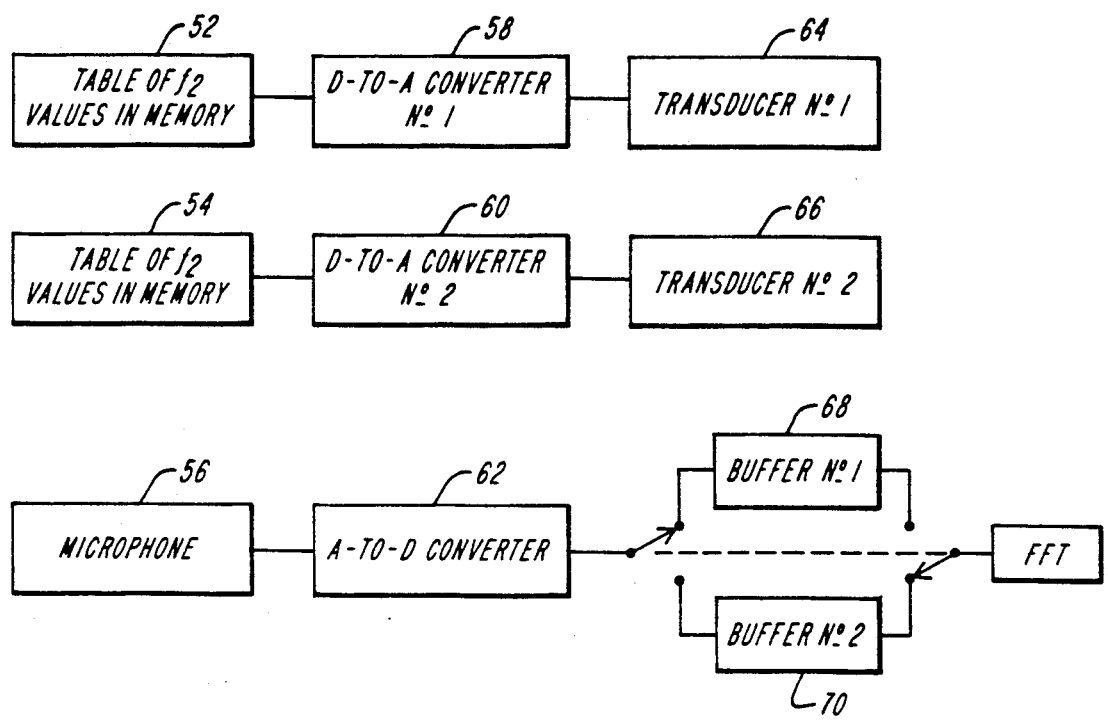
FIG. 6 is a schematic diagram of the functional components of one embodiment of the system of the present invention.

Referring to FIG. 3, the method for measuring hearing of the present invention will now be described. In step 20 a sample rate, $f_s$, and a power of 2, the latter to serve as the length L of an FFT, are chosen. In step 22, three (3) L-point buffers are established and zeros are placed in each location of each buffer. For purposes of this discussion, the buffers will be named Temp_0, Temp_1 and Perm. In step 24, frequencies of the primary pairs, where k is equal to the number of pairs, are selected from those discrete frequencies that result from choices of $f_s$ and L, namely, integer multiples of $f_s/L$. For example, if the chosen sample rate is 20,000 Hz and the value of L is selected as 1024, then the discrete analysis frequencies will be at integer multiples of 19.53 Hz.

In step 26, a table is then made and stored in a binary memory device containing the instantaneous values of L samples of the k selected $f_1$ tones, and in step 28 a second table of the instantaneous values of the k selected $f_2$ tones is created and stored. These tables are used to provide input signals to the two transducers 64, 66 which deliver the primary tones to the ear of the subject. Each of these two tables contains 1024 entries in this example and each entry in one table is the sum of the instantaneous values of the k $f_1$ (lower-frequency) tones of each pair, and the other table contains the sums of the instantaneous values of the k $f_2$ (higher-frequency) tones of each pair. The contribution of each frequency component to the sum is computed as follows:

$$\text{Value} = \sin(\text{sample number} \times \text{bin number} \times 2 \times PI/1024) \quad s[n] = A\sin(2\pi n j/L)$$

where s[n] is the amount to be added into the table for that sample number n is the location in the table, from 1 to 1024 j is the jth harmonic of $f_s/L$.

A is the desired amplitude.

The values in these tables are sequentially read and sent to digital-to-analog converters 58, 60 in step 32. The output of each converter is then the content of its respective table represented as an analog waveform, which is sent to the input terminals of an electrical-to-acoustic transducer 64, 66 in or near the entrance of the ear canal of the test subject. In accordance with the present invention, each of the two tables forms the input waveform to one of two independent transducers, thereby isolating and separating frequency components in the acoustic signal which could produce intermodulation distortion products in the transducers at the frequencies of distortion products of interest produced by the ear.

In step 36 a frame counter is used to keep track of the current frame number, for two purposes. First, it is used to alternate the buffers Temp_0 and Temp_1 between processing and sampling modes. Second, the counter is used to sense the end of a measurement when a prescribed number of frames have been processed. In step 38, the system samples L points of the signal from the microphone 56 via analog-to-digital converter 62. These points are stored in either buffer Temp_0 68 or Temp_1 70. The determination of which buffer is used depends upon whether the frame counter is an odd number or an even number. If the frame counter is odd, the values are stored in Temp_0 buffer 68 and if the frame counter is even, the sample points are stored in Temp_1 buffer 70. This allows the buffers to be used alternately and to be filled while the values in the other buffer are being processed.

In step 40 the system performs a fast Fourier transform on the signal stored in buffer Temp_J which is the buffer in which the sample L points are not being stored at the same time. In step 42 this L-point frame is analyzed for transient noise. This analysis is done by first computing the fast Fourier transform of the received frame and measuring the magnitudes of M frequency components surrounding the sought-after EDPs. A measure of transient noise can be, for example, the largest of these neighboring component magnitudes, or their RMS average. In step 44 if the detected transient noise exceeds a threshold, then the data in Temp_J buffer is discarded and the system waits for the sampling which results in points of the microphone signal being placed into Temp_I buffer in step 38 to be finished. If the transient noise does not exceed the threshold, the system in step 46 adds the complex FFT computed from the frame in the Temp_I buffer to existing values in the Perm buffer and then increments the frame counter. In step 47 the system checks if the desired number of valid frames has been reached, and if it has not, in step 48 it waits for the end of the filling of the Temp_I buffer with samples and then continues with execution in step 36. If the prescribed number of frames has been reached, the results are displayed in step 49 and the processing ends in step 50.

The acquisition of the acoustic signal in the case of the described example, based on FFTs which operate on 1024 samples, would be set up so as to alternately fill two buffers 68 and 70, each 1024 samples in length. The number of buffers, the sample rate, and the length of the FFT performed, while related, may be chosen to have values much different from those in the example given here, without departing from the nature of the present invention. When a Motorola DSP56001 digital signal processor chip is used to execute the FFT in step 40, the time taken to obtain the results of the FFT is less than the time needed to fill a buffer, and consequently, no data is acquired which is not analyzed. Obviously, any other digital signal processor that can execute a FFT at similar speed could be used. While an FFT is performed on the contents of one buffer, the other buffer is being filled from the output of the analog-to-digital converter.

An advantage of employing primary tones in the ratio 1:2:4...2n is that the intermodulation products formed in a single transducer delivering these tones to the ear fall at $nf_1 + mf_2$, n, m = 0, ±1, ±2, .... These distortion products are distinct from those of interest. While this ratio is therefore preferred there may be other combinations of multiple lower or upper primary tones that provide satisfactory results.

In the present invention, information may be obtained rapidly for a broad range of frequencies. Specifically, it has been found that as small a time period as a few seconds will suffice. A child tested in accordance with the present invention need only remain still for as little as a few seconds to permit completion of the entire test, where it is not uncommon for testing by measurement of numerous EDPs serially and individually to take five to ten minutes, or testing by the impulse/echo method to occupy a time period of several minutes. The present invention therefore has the potential capability of reducing the cost of hearing screening in clinics and hospitals, which would contribute to lowering health care costs.

The same procedures described above for the purpose of limiting the duration of the test to a necessary and sufficient time for reliable judgment of auditory function may be alternatively employed as a means of continuously and simultaneously monitoring the level of all of the EDPs evoked by a plurality of sets of primaries. Such monitoring may be of special value during some forms of surgery, for example, during such procedures as sectioning of the vestibular nerve, at which time it is desirable to observe continuously any alteration in auditory function that may be a result of surgical manipulations.

The above-described procedures, which could be terminated after a prescribed number of frames, could alternatively be terminated after specified criteria are reached. This adaptive stopping procedure would prevent continued testing after adequate information has become available regarding the functionality of the subject's hearing.

While the foregoing invention has been described with reference to its preferred embodiments, various alterations and modifications will occur to those skilled in the art. All such variations and modifications are intended to fall within the scope of the appended claims.

What is claimed is:

1. A method for testing hearing over a range of audible frequencies comprising the steps of:

simultaneously presenting a plurality of primary tones to an ear of a subject being tested through a first transducer, said primary tones being single-frequency sinusoidal tones and said plurality of primary tones including tones with different frequencies;

simultaneously presenting a plurality of primary tones in said ear through a second transducer said plurality of primary tones including tones with different frequencies;

measuring auditory distortion tones generated by pairs of said primary tones, each of said pairs of primary tones including one primary tone presented by said first transducer and one primary tone presented by said second transducer, said frequencies of said primary tones being selected to prevent the production of unwanted intermodulation distortion products.

2. The method for testing hearing over a range of audible frequencies of claim 1 wherein said plurality of primary tones presented by said first transducer are $f_1$ frequency primary tones, each of said $f_1$ primary tones being in a different location of the range of audible frequencies.

3. The method for testing hearing over a range of audible frequencies of claim 2 wherein said plurality of primary tones presented by said second transducer are $f_2$ frequency primary tones, each of said $f_2$ primary tones corresponding to an $f_1$ primary tone so as to make a ratio of such $f_1$ and $f_2$ primary tones suitable for the production of auditory distortion products.

4. The method for testing over a range of audible frequencies of claim 3 wherein the ratio of frequency $f_2$ to the frequency of $f_1$ is approximately 1.2.

5. A method for testing hearing over a range of audible frequencies of claim 1 further comprising the steps of:
  a) selecting a sample rate $f_s$ and a frame length L for use in the execution of a fast Fourier transform;
  b) sampling L points of a signal received by a microphone and storing said sampled L points in one of two buffers, said one buffer being alternatively selected so that the same buffer is not used for consecutive sampling steps;
  c) performing a fast Fourier transform (FFT) on the sampled L points stored in the other of said two buffers while sampled points are being stored concurrently in said one of two buffers;
  d) repeating steps (b) and (c) until the desired number of samples is obtained.

6. The method for testing hearing over a range of audible frequencies of claim 5 further comprising the steps of:
  analyzing the FFT spectrum for transient noise;
  discarding said sampled L points for which the transient noise of said FFT spectrum exceeds a preselected threshhold.

7. The method for testing hearing over a range of audible frequencies of claim 1 wherein the ratio of each frequency to any other frequency presented by one of said first and second transducers is 1 to $2^n$.

* * * * *